(12) United States Patent
Kurimoto et al.

(10) Patent No.: US 11,099,807 B2
(45) Date of Patent: Aug. 24, 2021

(54) ELECTRONIC APPARATUS, CONTROL DEVICE, CONTROL METHOD, AND RECORDING MEDIUM

(71) Applicant: SHARP KABUSHIKI KAISHA, Sakai (JP)

(72) Inventors: Yusuke Kurimoto, Sakai (JP); Hiroshi Wada, Sakai (JP); Hideaki Ohtsuki, Sakai (JP); Cheng Chang, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 62 days.

(21) Appl. No.: 16/786,401

(22) Filed: Feb. 10, 2020

(65) Prior Publication Data

US 2020/0264833 A1 Aug. 20, 2020

(30) Foreign Application Priority Data

Feb. 14, 2019 (JP) .............................. JP2019-024634

(51) Int. Cl.
*G06F 3/16* (2006.01)
*G10L 15/22* (2006.01)
*G10L 25/51* (2013.01)

(52) U.S. Cl.
CPC .............. *G06F 3/165* (2013.01); *G10L 15/22* (2013.01); *G10L 25/51* (2013.01)

(58) Field of Classification Search
CPC .......... G10L 25/51; G10L 15/22; G06F 3/165
See application file for complete search history.

(56) References Cited

U.S. PATENT DOCUMENTS

| | | | |
|---|---|---|---|
| 9,495,331 B2* | 11/2016 | Govrin | G06N 5/02 |
| 9,633,317 B2* | 4/2017 | Gabel | G06N 5/022 |
| 10,474,961 B2* | 11/2019 | Brigham | G06N 5/02 |
| 11,024,306 B2* | 6/2021 | Bhaya | G10L 15/1822 |
| 2002/0081937 A1 | 6/2002 | Yamada et al. | |
| 2017/0076212 A1* | 3/2017 | Shams | G06N 5/04 |
| 2018/0176269 A1* | 6/2018 | Griffin | H04L 65/403 |
| 2019/0228766 A1* | 7/2019 | White | G06Q 10/109 |

FOREIGN PATENT DOCUMENTS

JP 2002-307354 A 10/2002

* cited by examiner

*Primary Examiner* — Mohammad K Islam
(74) *Attorney, Agent, or Firm* — ScienBiziP, P.C.

(57) ABSTRACT

Provided is an electronic apparatus including: at least one voice output device; and at least one control device, in which the control device performs event detection processing by which occurrence of a predetermined event is detected, confirmation processing by which whether or not data to be input in association with the event by a user is stored in a storage device is confirmed, voice urging data preparation processing by which, in a case where the data is not stored in the storage device, voice urging data that urges the user to input the data is prepared, and voice output processing by which the voice urging data is output from the voice output device.

4 Claims, 4 Drawing Sheets

ELECTRONIC APPARATUS, CONTROL DEVICE, CONTROL METHOD, AND RECORDING MEDIUM

BACKGROUND

1. Field

The present disclosure relates to an electronic apparatus, a control device, a control method, and a recording medium.

2. Description of the Related Art

Conventionally, there have been many health care applications aiming at diet or health management. When data about a weight, a meal, or the like is input to a smartphone, various proposals on a meal menu, an exercise menu, or the like are offered to a user. Moreover, in Japanese Unexamined Patent Application Publication No. 2002-307354, an electronic toy that detects occurrence of an event in a life rhythm on a specific person and selects a control parameter of at least any of a movement mechanism, an information display unit, and a sound generation unit in accordance with the event is disclosed.

However, in order that various proposals on a meal menu, an exercise menu, or the like are offered, a user is requested to input data of, for example, a weight, a meal, or the like to an electronic apparatus every day. In a daily life, the user forgets inputting such daily data in some cases. When the user forgets inputting the data, appropriate service such as various proposals on a meal menu or an exercise menu is difficult to be offered.

In a case of a health care application installed in a smartphone or the like, although display that urges a user to input data is executed, there is a problem that the user forgets inputting the data, since the user does not always look at the smartphone. An aspect of the disclosure enables a user to input data without forgetting and provides better service to the user on the basis of the input of the data.

SUMMARY

In order to deal with the aforementioned problem, an electronic apparatus according to an aspect of the disclosure is an electronic apparatus including: at least one voice output device; and at least one control device, in which the control device performs event detection processing by which occurrence of a predetermined event is detected, confirmation processing by which whether or not data to be input in association with the event by a user is stored in a storage device is confirmed, voice urging data preparation processing by which, in a case where the data is not stored in the storage device, voice urging data that urges the user to input the data is prepared, and voice output processing by which the voice urging data is output from the voice output device.

Moreover, a control device according to an aspect of the disclosure is a control device that controls an electronic apparatus including at least one voice output device, and includes: an event detection unit that performs processing by which occurrence of a predetermined event is detected; a confirmation unit that performs processing by which whether or not data to be input in association with the event by a user is stored in a storage device is confirmed; a voice urging data preparation unit that performs processing by which, in a case where the data is not stored in the storage device, voice urging data that urges the user to input the data is prepared; and a voice output unit that performs processing by which the voice urging data is output from the voice output device.

Further, a control method according to an aspect of the disclosure is a control method by which an electronic apparatus including at least one voice output device is controlled, and includes: detecting occurrence of a predetermined event; confirming whether or not data to be input in association with the event by a user is stored in a storage device; preparing, in a case where the data is not stored in the storage device, voice urging data that urges the user to input the data; and outputting the voice urging data from the voice output device.

DESCRIPTION OF THE EMBODIMENTS

[Embodiment]
(Configuration of Electronic Apparatus 1)

Figure 1:
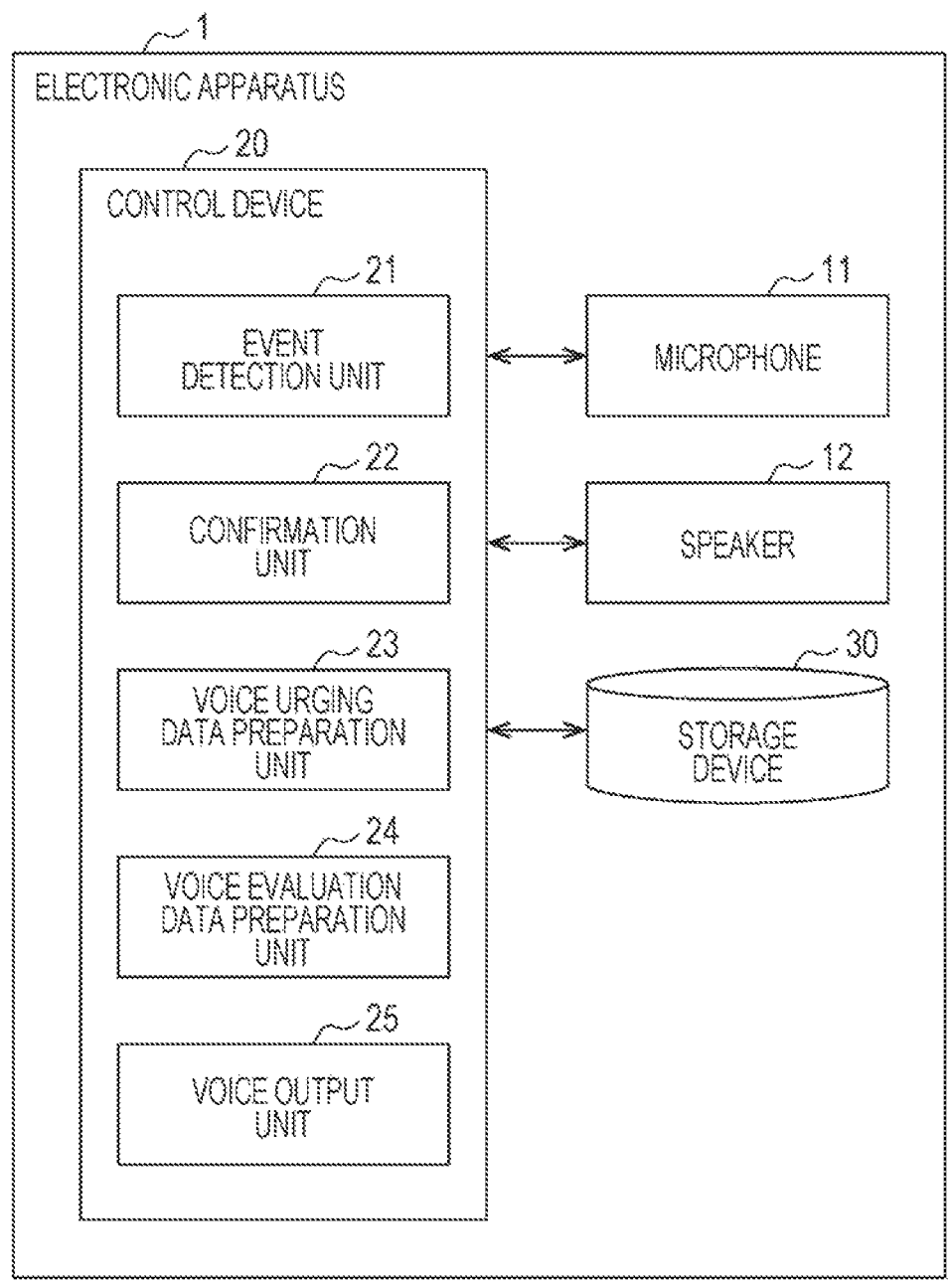
FIG. 1 is a block diagram illustrating a configuration of an electronic apparatus according to an embodiment of the disclosure.

A configuration of an electronic apparatus 1 will be described on the basis of FIG. 1. FIG. 1 is a block diagram illustrating the configuration of the electronic apparatus 1 according to an embodiment of the disclosure. As illustrated in FIG. 1, the electronic apparatus 1 includes at least one microphone 11, at least one speaker 12 (voice output device), at least one control device 20, and at least one storage device 30. That is, the number of each of microphones 11, speakers 12, control devices 20, and storage devices 30 may be single or may be plural. The electronic apparatus 1 may be a robot capable of having a conversation with a user, but is not limited thereto, and may be, for example, a smartphone or the like which includes a conversation function.

The microphone 11 functions as a voice input device that inputs a voice from the user. The microphone 11 is a voice collection device such as a conventional and general microphone. The microphone 11 converts the input voice into an electric signal and outputs the resultant to the control device 20. The control device 20 performs voice recognition for the input voice and then judges an instruction content from the user. Note that, the voice recognition for the input voice may be performed not by the control device 20 but by, for example, a member that is provided in the electronic apparatus 1 and exclusively for the voice recognition.

According to an aspect in which an instruction is input to the electronic apparatus 1 by a voice of the user in this manner, the user is able to easily give an instruction only by talking to the electronic apparatus 1. Note that, the input to the electronic apparatus 1 from the user is not limited to be performed with use of the voice but may be performed with use of a touch panel, a keyboard, or the like or with use of, for example, recognition of movement (gesture) of the user by a camera or the like. According to such a configuration, the user is able to give an instruction to the electronic apparatus 1 even in a situation, such as a quiet public space, in which it is difficult to speak.

The speaker 12 outputs a voice from the electronic apparatus 1 and is connected to the control device 20. The speaker 12 is a conventional and general voice output device. The electronic apparatus 1 recognizes an instruction of the user with use of the voice of the user, which is input via the microphone 11, or the like and provides service with use of the voice via the speaker 12, and thereby achieves the conversation function between the electronic apparatus 1 and the user.

(Control Device 20)

The control device 20 is, for example, a CPU (Central Processing Unit), and integrally controls each unit of the electronic apparatus 1. That is, the control device 20 is a device that controls the electronic apparatus 1. The control device 20 includes an event detection unit 21, a confirmation unit 22, a voice urging data preparation unit 23, a voice evaluation data preparation unit 24, and a voice output unit 25.

The event detection unit 21 performs processing (event detection processing) by which occurrence of a predetermined event is detected. Examples of the predetermined event include an input of meal data, an input of weight data, an input of the number of steps, a state before going out, a state at a time of coming home, and a state before sleeping. That is, the predetermined event is an input operation to the electronic apparatus 1 by the user or a state judged on the basis of the present time. The inputs of meal data, weight data, and the number of steps respectively indicate inputs of meal data, weight data, and the number of steps, which are performed to the electronic apparatus 1 by the user. As above, the event detection unit 21 detects timing of daily activities of the user.

The state before going out indicates a state where the present time becomes time a given time before time when the user goes out. The state at the time of coming home indicates a state where the present time becomes time when the user comes home. The state before sleeping indicates a state where the present time becomes time a given time before time when the user sleeps. The time when the user goes out, the time when the user comes home, and the time when the user sleeps are stored in the storage device 30 in advance.

The confirmation unit 22 performs processing (confirmation processing) by which whether or not data to be input in association with an event by the user is stored in the storage device 30 is confirmed in accordance with a correspondence relation between an event and data to be input by the user. Examples of the data to be input in association with an event by the user include a meal menu, a weight, the number of steps, a height, an age, and a sex. The above-described correspondence relation will be described later.

In a case where the data to be input in association with an event by the user is not stored in the storage device 30, the voice urging data preparation unit 23 performs processing (voice urging data preparation processing) by which voice urging data that urges the user to input the data is prepared. Examples of the voice urging data include data that urges the user to input a meal menu, a meal calorie, a weight, the number of steps, a height, an age, and a sex. The voice output unit 25 performs processing (voice output processing) by which the voice urging data prepared by the voice urging data preparation unit 23 is output from the speaker 12.

For input data that is input by the user in response to the output of the voice urging data, the voice evaluation data preparation unit 24 performs processing (voice evaluation data preparation processing) by which voice evaluation data that evaluates the input data is prepared by referring to data that has been input in the past by the user and stored in the storage device 30.

Note that, the control device 20 may be provided in the electronic apparatus 1, or may be provided in a cloud server. In the latter case, a communication device (not illustrated) provided in the electronic apparatus 1 may transmit a voice of the user to the control device 20 in the cloud server. In this case, the control device 20 in the cloud server may perform each processing described above on the basis of the voice and transmit voice data, which is to be output by the voice output unit 25, to the electronic apparatus 1. According to this configuration, the electronic apparatus 1 is not required to include the control device 20, and it is possible to manufacture the electronic apparatus 1 at a low cost. Moreover, the control device 20 that has higher performance than that of the control device 20 provided in the electronic apparatus 1 is able to be provided in the cloud server.

(Storage Device 30)

The storage device 30 stores information of an input of data from the user, or the like. Examples of the storage device 30 include an HDD (Hard Disk Drive), an SSD (Solid State Drive), and a ROM (Read Only Memory). Moreover, the storage device 30 may further include, for example, a RAM (Random Access Memory) which develops a program or the like that is executed in the electronic apparatus 1.

The correspondence relation between an event and data to be input by the user is stored in the storage device 30 in advance. That is, an event and data to be input by the user are associated in advance. For example, it is assumed that, in a case where an event is "the input of meal data", data associated with "the input of meal data" serving as the event is "a weight". In this case, "the input of meal data" serving as the event and "the weight" serving as the data to be input by the user are stored in the storage device 30 in an associated manner.

Note that, in the aforementioned correspondence relation, at least one of the number of events and the number of pieces of data to be input by the user may be plural. For example, in a case where an event is "the state before going out", data to be input by the user may be "a meal menu" and "a meal calorie".

(Example of Processing by Control Device 20)

Figure 2:
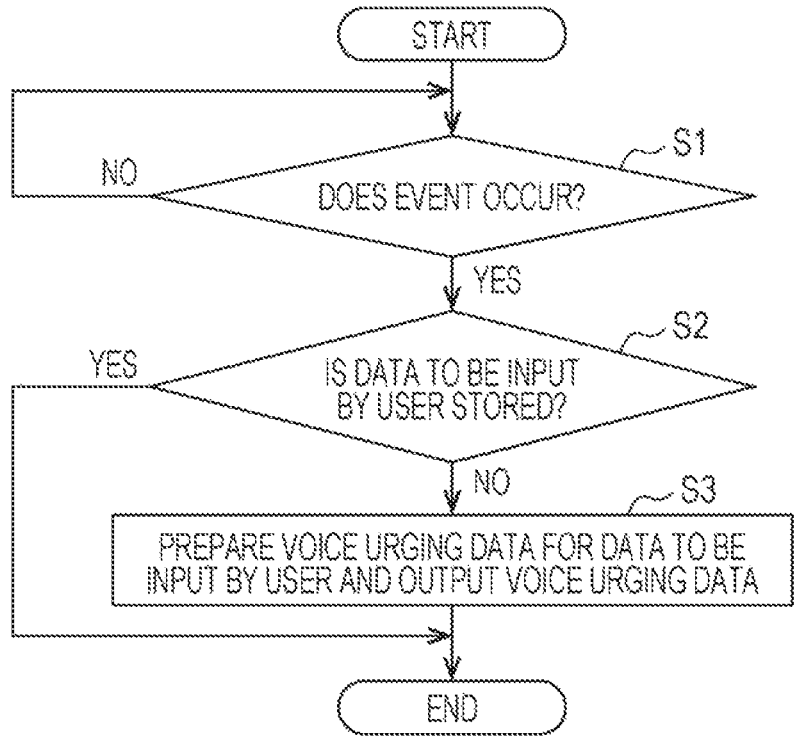
FIG. 2 is a flowchart illustrating an example of a flow of processing by a control device that is provided in the electronic apparatus illustrated in FIG. 1.
Figure 3:
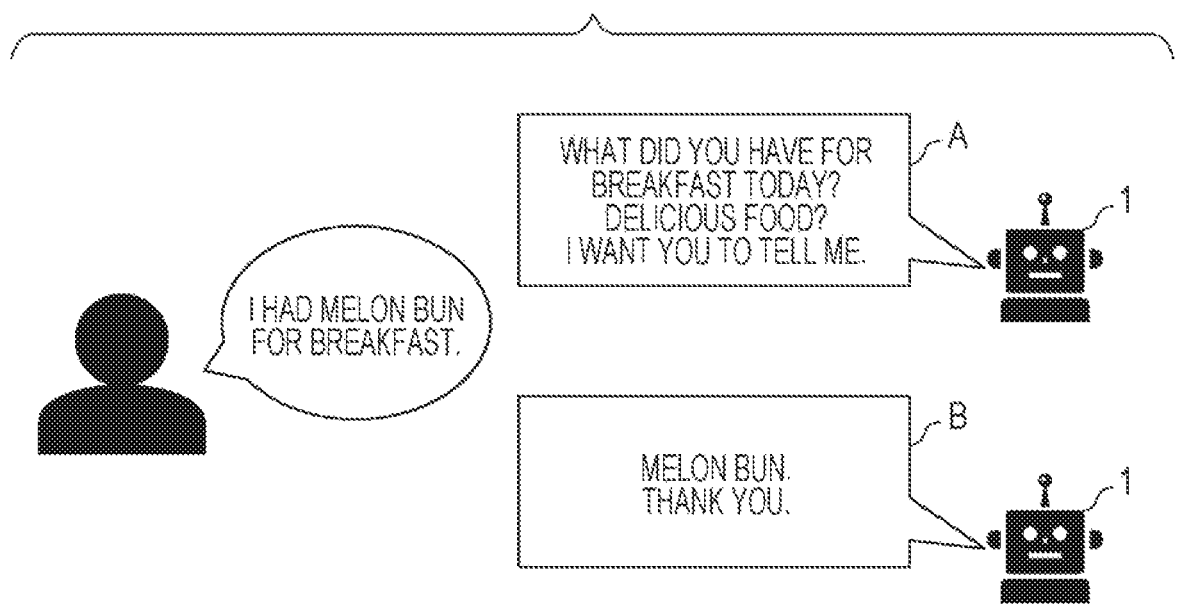
FIG. 3 is a view illustrating an example of a conversation by the electronic apparatus illustrated in FIG. 1.

An example of processing (control method) by the control device 20 will be described with reference to FIGS. 2 and 3. FIG. 2 is a flowchart illustrating an example of a flow of the processing by the control device 20 that is provided in the electronic apparatus 1 illustrated in FIG. 1. FIG. 3 is a view illustrating an example of a conversation by the electronic apparatus 1 illustrated in FIG. 1. As illustrated in FIG. 2, first, the event detection unit 21 confirms whether or not a predetermined event occurs (step S1).

When the event detection unit 21 does not detect that the predetermined event occurs (in a case of NO at step S1), the event detection unit 21 continues the processing of step S1. When the event detection unit 21 detects that the predetermined event occurs (in a case of YES at step S1: event detection step), the confirmation unit 22 performs processing by which whether or not data to be input in association with the event by a user is stored in the storage device 30 is confirmed in accordance with the correspondence relation between an event and data to be input by the user (step S2: confirmation step). Description will be given below specifically.

It is assumed here that the predetermined event is "the state before going out". At a time point when the present time becomes time a given time before time when the user goes out, the event detection unit 21 detects that "the state before going out" serving as the predetermined event occurs. The confirmation unit 22 refers to, from the storage device 30, the correspondence relation between an event and data to be input by the user and thereby recognizes that data associated with "the state before going out" serving as the event is "a meal menu". The confirmation unit 22 performs processing by which whether or not data corresponding to "the meal menu" is stored in the storage device 30 is confirmed.

Note that, when the confirmation unit 22 performs the processing of step S2, the confirmation unit 22 may confirm whether or not the data to be input by the user is stored in the storage device 30, by referring only to data, which is stored in the latest given period, in data stored in the storage device 30. Thereby, for example, the confirmation unit 22 is able to confirm, as to the latest event, whether or not the data to be input by the user is stored in the storage device 30.

That is, a target of the data to be input by the user is able to be limited to one which is related to the latest event. For example, in a case where the data to be input by the user is "a meal menu" about breakfast of one day, it is possible to set "a meal menu" about breakfast of another day not to be the target.

When the data to be input in association with the event by the user is stored in the storage device 30 (in a case of YES at step S2), the processing by the control device 20 ends. A case where the data to be input in association with the event by the user is not stored in the storage device 30 (case of NO at step S2) is considered. In this case, the voice urging data preparation unit 23 performs processing by which voice urging data that urges the user to input the data to be input by the user is prepared, and the voice output unit 25 performs processing by which the voice urging data is output from the speaker 12 (step S3: voice urging data preparation step, voice output step).

For example, a case where the data corresponding to "the meal menu" is not stored in the storage device 30 is considered. In this case, the voice urging data preparation unit 23 prepares voice urging data by which an action A illustrated in FIG. 3 is performed. The action A includes a content that urges the user to input "the meal menu". The voice urging data preparation unit 23 provides the prepared voice urging data to the voice output unit 25.

Here, the voice urging data may be prepared when the voice urging data preparation unit 23 refers to a data table in which voice data which is linked with data to be input by the user and corresponds to each content of the data is stored. Moreover, artificial intelligence (AI) may be incorporated in the electronic apparatus 1, the artificial intelligence may generate appropriate voice data corresponding to data to be input by the user, and the voice urging data preparation unit 23 may perform preparation by using the generated voice data as the voice urging data. The voice evaluation data may be also prepared by a method similar to the preparation method of the voice urging data, which is described here.

The voice output unit 25 performs processing by which the voice urging data provided from the voice urging data preparation unit 23 is output from the speaker 12. When the speaker 12 outputs the voice urging data as a voice, the action A is performed. As illustrated in FIG. 3, when the user inputs "the meal menu" in the electronic apparatus 1 after the action A is performed, the control device 20 stores "the meal menu", which is input from the microphone 11, in the storage device 30. Moreover, when the control device 20 prepares voice data for a reply to the user and outputs the prepared voice data from the speaker 12, an action B is performed.

As above, the electronic apparatus 1 outputs the voice urging data that urges the user to input data, so that the user is able to input the data without forgetting. Thus, the electronic apparatus 1 is able to provide better service to the user on the basis of the input of the data.

Modified Example 1

Figure 4:
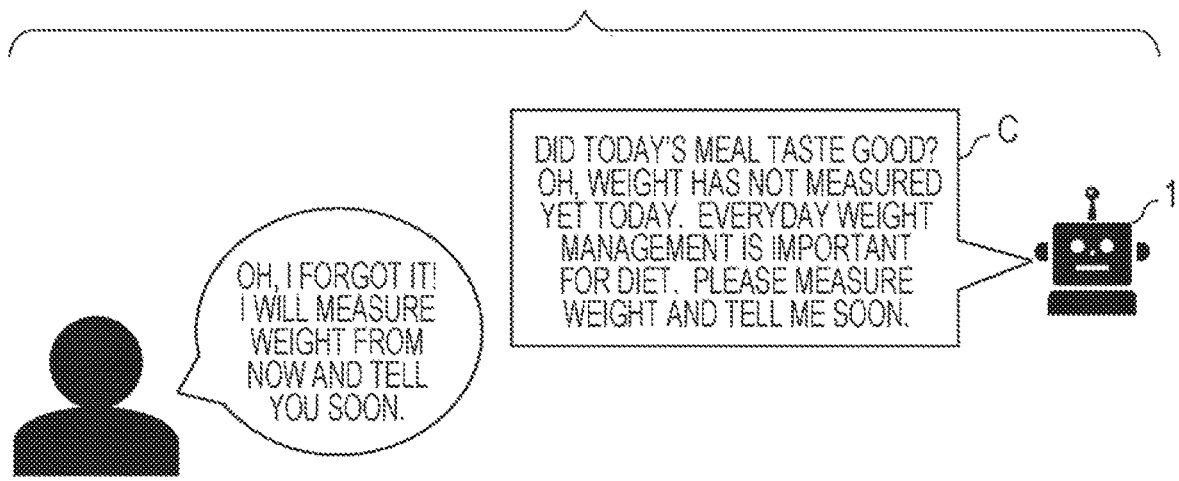
FIG. 4 is a view illustrating an example of a conversation by the electronic apparatus illustrated in FIG. 1.

A modified example 1 of the processing by the control device 20 will be described with reference to FIG. 4. FIG. 4 is a view illustrating an example of a conversation by the electronic apparatus 1 illustrated in FIG. 1. At step S3 described above, the voice urging data preparation unit 23 may prepare voice urging data so as to include a voice that informs a user of importance of an input of data. Description will be given below specifically.

It is assumed here, for example, that a predetermined event detected by the event detection unit 21 is "the input of meal data". Moreover, a case where data corresponding to "a weight" serving as data to be input by the user is not stored in the storage device 30 is considered. In this case, at step S3 described above, the voice urging data preparation unit 23 prepares voice urging data by which an action C illustrated in FIG. 4 is performed.

The action C includes a content that urges the user to input "the weight" and a content that informs the user of importance of the input of "the weight". The voice urging data preparation unit 23 provides the prepared voice urging data to the voice output unit 25.

The voice output unit 25 performs processing by which the voice urging data provided from the voice urging data preparation unit 23 is output from the speaker 12. When the speaker 12 outputs the voice urging data as a voice, the action C is performed. According to this configuration, it is possible to notify the user of importance of an input of data, thus making it possible to increase a possibility that the user inputs the data.

Modified Example 2

Figure 5:
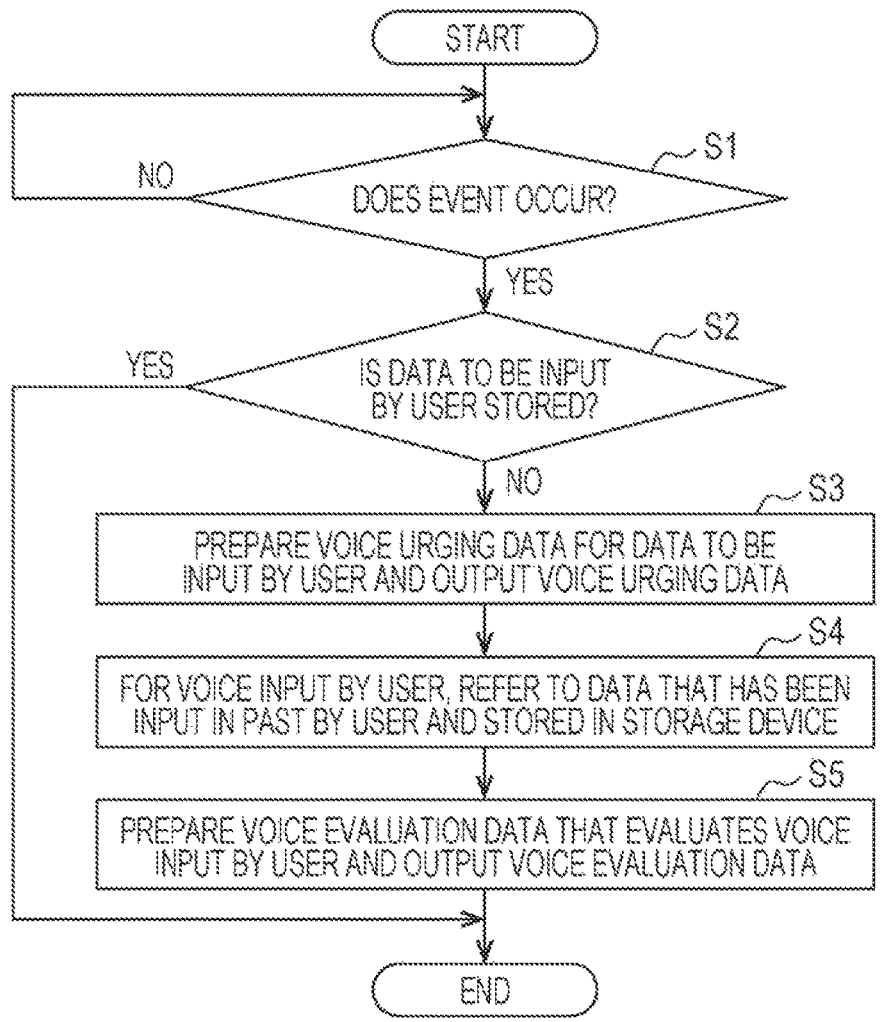
FIG. 5 is a flowchart illustrating a modified example of the flow of the processing by the control device that is provided in the electronic apparatus illustrated in FIG. 1.
Figure 6:
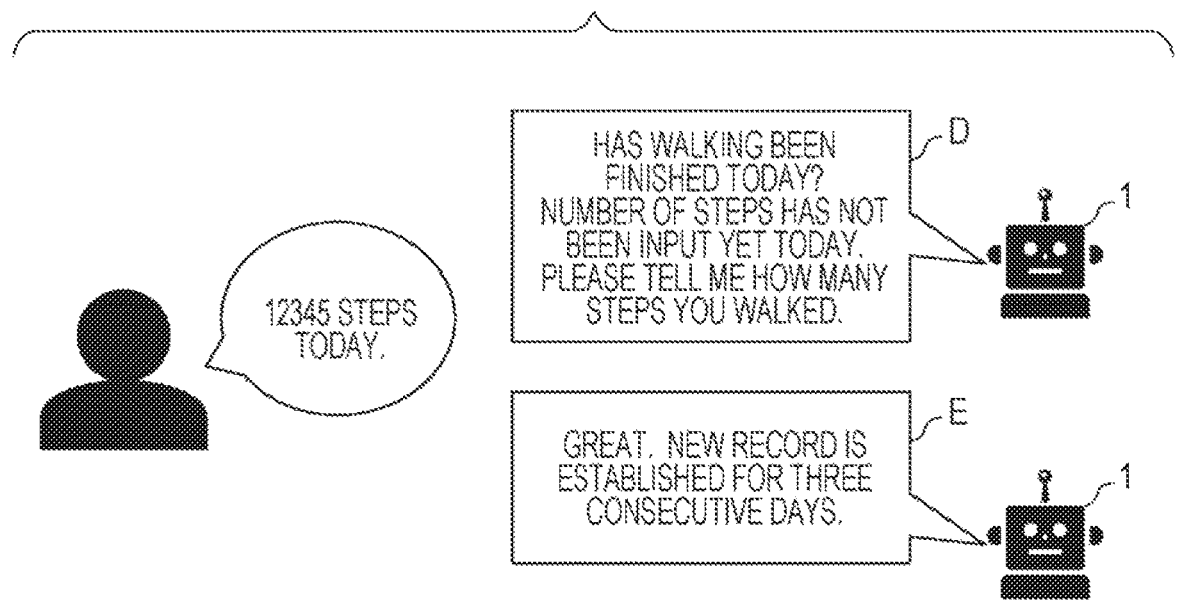
FIG. 6 is a view illustrating an example of a conversation by the electronic apparatus illustrated in FIG. 1.
Figure 7:
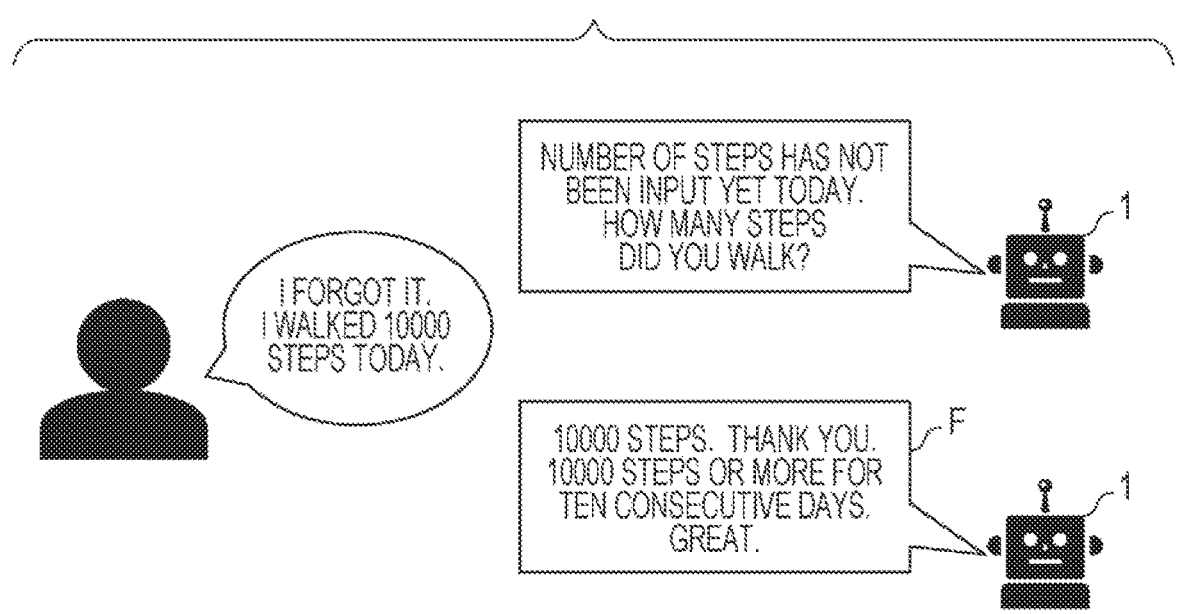
FIG. 7 is a view illustrating an example of a conversation by the electronic apparatus illustrated in FIG. 1.

A modified example 2 of the processing by the control device 20 will be described with reference to FIGS. 5 to 7. FIG. 5 is a flowchart illustrating the modified. example of the flow of the processing by the control device 20 that is provided in the electronic apparatus 1 illustrated in FIG. 1. FIGS. 6 and 7 are views each illustrating an example of a conversation by the electronic apparatus 1 illustrated in FIG. 1. As illustrated in FIG. 5, first, the above-described processing of step S1 and step S2 is performed.

It is assumed here, for example, that a predetermined event detected by the event detection unit 21 is "the state before sleeping". At a time point when the present time becomes time a given time before time when a user sleeps, the event detection unit 21 detects that "the state before sleeping" serving as the predetermined event occurs.

Further, a case where data corresponding to "the number of steps" is not stored in the storage device 30 is considered. In this case, the voice urging data preparation unit 23 prepares voice urging data by which an action D illustrated in FIG. 6 is performed. The action D includes a content that confirms, to the user, whether or not walking is completed and a content that urges the user to input "the number of steps". The voice urging data preparation unit 23 provides the prepared voice urging data to the voice output unit 25.

The voice output unit 25 performs processing by which the voice urging data provided from the voice urging data preparation unit 23 is output from the speaker 12 (step S3). When the speaker 12 outputs the voice urging data as a voice, the action D is performed. As illustrated in FIG. 6, when the user inputs "the number of steps" in the electronic apparatus 1 after the action D is performed, the control device 20 stores "the number of steps", which is input from the microphone 11, in the storage device 30.

For the input data input by the user, the voice evaluation data preparation unit 24 refers to data that has been input in the past by the user and stored in the storage device 30 (step S4). Specifically, for "the number of steps" as information that is included in the input data input by the user, the voice evaluation data preparation unit 24 refers to "the number of steps" that has been input in the past by the user and stored in the storage device 30.

Here, for example, the voice evaluation data preparation unit 24 compares "the number of steps" as the information included in the input data that is input this time by the user and "the number of steps" that has been input in the past by the user and stored in the storage device 30. In a case where "the number of steps" as the information included in the input data that is input this time by the user is larger than "the number of steps" that has been input by the user one day before or two days before and stored in the storage device 30, the voice evaluation data preparation unit 24 prepares voice evaluation data by which an action E illustrated in FIG. 6 is performed.

The action E includes a content that notifies the user that a new record of "the number of steps" is established for three consecutive days. The voice evaluation data preparation unit 24 provides the prepared voice evaluation data to the voice output unit 25. The voice output unit 25 performs processing by which the voice evaluation data provided from the voice evaluation data preparation unit 24 is output from the speaker 12 (step S5). When the speaker 12 outputs the voice evaluation data as a voice, the action E is performed.

Note that, the voice evaluation data preparation unit 24 may prepare voice evaluation data so that an action F illustrated in FIG. 7 is performed. Specifically, the voice evaluation data preparation unit 24 confirms whether or not "the number of steps" as the information included in the input data that is input this time by the user is equal to or more than 10000 steps.

Moreover, in a case where "the number of steps" input this time and "the numbers of steps" that have been input one to nine days before by the user and stored in the storage device 30 are each equal to or more than 10000 steps, the voice evaluation data preparation unit 24 recognizes that "the numbers of steps" are each equal to or more than 10000 steps for ten consecutive days. In this case, the voice evaluation data preparation unit 24 prepares voice evaluation data by which the action F illustrated in FIG. 7 is performed. The action F includes a content that notifies the user that "the numbers of steps" are each equal to or more than 10000 steps for 10 consecutive days. Thereafter, the action F is performed similarly to the action E.

In this manner, for the input data that is input by the user in response to the output of the voice urging data, the voice evaluation data preparation unit 24 performs processing by which voice evaluation data that evaluates the input data is prepared by referring to data that has been input in the past by the user and stored in the storage device 30. Thereby, the input data input by the user is evaluated, so that it is possible to cause the user to recognize the evaluation. Therefore, it is possible to enhance motivation of the user and increase a possibility that the user inputs the data.

[Implementation Example by Software]

Control blocks (particularly, the event detection unit 21, the confirmation unit 22, the voice urging data preparation unit 23, the voice evaluation data preparation unit 24, and the voice output unit 25) of the control device 20 may be implemented by a logic circuit (hardware) formed in an integrated circuit (IC chip) or the like or may be implemented by software.

In the latter case, the control device 20 includes a computer that executes a command of a program that is software implementing each function. The computer includes, for example, at least one processor (control device) and at least one computer-readable recording medium that stores the program. When the processor reads the program from the recording medium and executes the program in the computer, the disclosure is implemented. As the processor, for example, a CPU (Central Processing Unit) is able to be used. As the recording medium, a "non-transitory tangible medium", for example, such as a tape, a disk, a card, a semiconductor memory, or a programmable logic circuit is able to be used in addition to a ROM (Read Only Memory) and the like. Moreover, a RAM (Random Access Memory), which develops the program, or the like may be further included. Further, the program may be supplied to the computer via any transmission medium (such as a communication network or a broadcast wave) which allows the program to be transmitted. Note that, an aspect of the disclosure can also be implemented in a form of a data signal in which the program is embodied through electronic transmission and which is embedded in a carrier wave.

[Conclusion]

An electronic apparatus according to an aspect 1 of the disclosure is an electronic apparatus including: at least one voice output device; and at least one control device, and has a configuration in which the control device performs event detection processing by which occurrence of a predetermined event is detected, confirmation processing by which whether or not data to be input in association with the event by a user is stored in a storage device is confirmed, voice urging data preparation processing by which, in a case where the data is not stored in the storage device, voice urging data that urges the user to input the data is prepared, and voice output processing by which the voice urging data is output from the voice output device.

The electronic apparatus according to an aspect 2 of the disclosure may have a configuration in which, in the aspect 1, the control device prepares the voice urging data so as to include a voice that informs the user of importance of the input of the data, in the voice urging data preparation processing.

The electronic apparatus according to an aspect 3 of the disclosure may have a configuration in which, in the aspect 1 or 2, the control device further performs voice evaluation data preparation processing by which, for input data input by the user in response to the output of the voice urging data, data that has been input in past by the user and stored in the storage device is referred to and voice evaluation data that evaluates the input data is prepared.

A control device according to an aspect 4 of the disclosure is a control device that controls an electronic apparatus including at least one voice output device, and has a configuration in which an event detection unit that performs processing by which occurrence of a predetermined event is detected; a confirmation unit that performs processing by which whether or not data to be input in association with the event by a user is stored in a storage device is confirmed; a voice urging data preparation unit that performs processing by which, in a case where the data is not stored in the storage device, voice urging data that urges the user to input the data is prepared; and a voice output unit that performs processing by which the voice urging data is output from the voice output device are included.

A control method according to an aspect 5 of the disclosure is a control method by which an electronic apparatus including at least one voice output device is controlled, and includes: detecting occurrence of a predetermined event; confirming whether or not data to be input in association with the event by a user is stored in a storage device; preparing, in a case where the data is not stored in the storage device, voice urging data that urges the user to input the data; and outputting the voice urging data from the voice output device.

The control device according to each of the aspects of the disclosure may be implemented by a computer. In this case, a program of the control device, which causes the computer to operate as each unit (software element) included in the control device to thereby achieve the control device by the computer, and a computer-readable recording medium that records the program are also encompassed in the scope of the disclosure.

[Additional Matter]

The disclosure is not limited to each of the embodiments described above and may be modified in various manners within the scope indicated in the claim, and an embodiment achieved by appropriately combining techniques disclosed in each of different embodiments is also encompassed in the technical scope of the disclosure. Further, by combining the techniques disclosed in each of the embodiments, a new technical feature may be formed.

The present disclosure contains subject matter related to that disclosed in Japanese Priority Patent Application JP 2019-024634 filed in the Japan Patent Office on Feb. 14, 2019, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An electronic apparatus comprising: at least one voice output device; and at least one control device, wherein the control device performs event detection processing by which occurrence of a predetermined event is detected, confirmation processing by which whether or not data to be input in association with the event by a user is stored in a storage device is confirmed, voice urging data preparation processing by which, in a case where the data is not stored in the storage device, voice urging data that urges the user to input the data is prepared, and voice output processing by which the voice urging data is output from the voice output device; wherein the control device prepares the voice urging data so as to include a voice that informs the user of importance of the input of the data, in the voice urging data preparation processing; wherein the control device further performs voice evaluation data preparation processing by which, for input data input by the user in response to the output of the voice urging data, data that has been input in past by the user and stored in the storage device is referred to and voice evaluation data that evaluates the input data is prepared.

2. A control device that controls an electronic apparatus including at least one voice output device, comprising: an event detection unit that performs processing by which occurrence of a predetermined event is detected; a confirmation unit that performs processing by which whether or not data to be input in association with the event by a user is stored in a storage device is confirmed; a voice urging data preparation unit that performs processing by which, in a case where the data is not stored in the storage device, voice urging data that urges the user to input the data is prepared; and a voice output unit that performs processing by which the voice urging data is output from the voice output device wherein the control device prepares the voice urging data so as to include a voice that informs the user of importance of the input of the data, in the voice urging data preparation processing; wherein the control device further performs voice evaluation data preparation processing by which, for input data input by the user in response to the output of the voice urging data, data that has been input in past by the user and stored in the storage device is referred to and voice evaluation data that evaluates the input data is prepared.

3. A control method by which an electronic apparatus including at least one voice output device is controlled, the control method comprising: detecting occurrence of a predetermined event; confirming whether or not data to be input in association with the event by a user is stored in a storage device; preparing, in a case where the data is not stored in the storage device, voice urging data that urges the user to input the data; and outputting the voice urging data from the voice output device wherein the control device prepares the voice urging data so as to include a voice that informs the user of importance of the input of the data, in the voice urging data preparation processing; wherein the control device further performs voice evaluation data preparation processing by which, for input data input by the user in response to the output of the voice urging data, data that has been input in past by the user and stored in the storage device is referred to and voice evaluation data that evaluates the input data is prepared.

4. A computer-readable recording medium that records a program by which a computer is caused to execute each process according to claim 3.

* * * * *